United States Patent [19]

Duffett

[11] Patent Number: Plant 6,615

[45] Date of Patent: Feb. 21, 1989

[54] CHRYSANTHEMUM PLANT NAMED RAYA

[75] Inventor: William E. Duffett, Salinas, Calif.

[73] Assignee: Yoder Brothers, Inc., Barberton, Ohio

[21] Appl. No.: 94,736

[22] Filed: Sep. 9, 1987

[51] Int. Cl.[4] ..... A01H 5/00

[52] U.S. Cl. ..... Plt./74

[58] Field of Search ..... Plt./74–82

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Raya particularly characterized by its flat capitulum form; spoon daisy capitulum type; white ray floret color; diameter across face of capitulum of up to 13 cm at maturity when grown as a pinched disbudded pot mum; uniform eight week photoperiodic flowering response to short days; medium plant height when grown as a pinched pot mum; excellent tolerance to high and low temperatures; recommended as disbudded pot mum; and semi-spreading branching pattern.

3 Drawing Sheets

1

The present invention comprises a new and distinct cultivar of Chrysanthemum, botanically known as *Chrysanthemum morifolium,* Ramat., and referred to by the cultivar name Raya.

Raya, identified as 79U42007, was originated from a cross made by William E. Duffett in a controlled breeding program in Salinas, Calif. in 1979.

The female parent of Raya was the cultivar Quills, disclosed in U.S. Plant Pat. No. 4,401. The male parent of Raya was an unnamed seedling identified as 79#02995.

Raya was discovered and selected as one flowering plant within the progeny of the stated cross by William E. Duffett in November of 1980, in a controlled environment in Salinas, Calif.

The first act of asexual reproduction of Raya was accomplished when vegetative cuttings were taken from the initial selection in February of 1981 in a controlled environment in Salinas, Calif., by technicians working under formulations established and supervised by William E. Duffett.

Horticultural examination of controlled flowerings of successive plantings has shown that the unique combination of characteristics as herein disclosed for Raya are firmly fixed and are retained through successive generations of asexual reproduction.

Raya has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Raya, which, in combination, distinguish this Chrysanthemum as a new and distinct cultivar:

1. Flat capitulum form.
2. Spoon daisy capitulum type.
3. White ray floret color.
4. Diameter across face of capitulum up to 13 cm at maturity, when grown as a pinched disbudded pot mum.

2

5. Uniform eight week photoperiodic flowering response to short days.
6. Medium plant height requiring 0 to 7 long days after pinch prior to short days and 1 application of 2500 ppm B-9 SP to attain a flowered plant height of 25 to 35 cm for year-round flowerings when grown as a pinched pot mum.
7. Excellent tolerance to high and low temperatures.
8. Recommended as disbudded pot mum.
9. Semi-spreading branching pattern.

The accompanying photographic drawings show typical inflorescence and leaf characteristics of Raya, with the colors being as nearly true as possible with illustrations of this type. Sheet 1 is a color photograph of Raya grown as a pinched disbudded pot mum. Sheet 2 is a black and white photograph of three views of the inflorescence of Raya. Sheet 3 is a black and white photograph showing the upper and under sides of the leaves of Raya at three stages of development (mature, intermediate and immature).

Of the commercial cultivars known to the inventor, the most similar in comparison to Raya is Quills, disclosed in U.S. Plant Pat. No. 4,401. Reference is made to attached Chart A, which compares certain characteristics of Raya to the same characteristics of Quills.

Similar traits are ray floret color, capitulum form and type, and plant height. Raya has a more spreading branching pattern, a much larger diameter of capitulum, and a slower flowering response to short days than Quills. Raya is recommended as a disbud pot mum. Quills is recommended as a pot disbud and spray pot mum.

In the following description, color references are made to the Royal Horticultural Society Colour Chart. The clear white color of the open spoon ends of the ray florets is not represented in the RHS Colour Chart. The color values were determined on plant material grown as a pinched disbudded pot mum in Salinas, Calif. on June 1, 1987.

Classification:

*Botanical.*—*Chrysanthemum morifolium,* Ramat., cv. Raya.

*Commercial.*—Spoon daisy disbud pot mum.

INFLORESCENCE

A. Capitulum:

*Form.*—Flat.

*Type.*—Spoon daisy.

*Diameter across face.*—Up to 13 cm at maturity.

B. Corolla of ray florets:

*Color (general tonality from a distance of three meters).*—White.

*Color (upper surface) (spoon tips).*—White.

*Color (under surface) (tubes).*—155A to 155B.

*Shape.*—Base tubular. Distal portion open, flattened and spoon like.

C. Corolla of disc florets:

*Color (mature).*—Closest to 1A.

*Color (immature).*—Closest to 144A to 144B.

D. Reproductive organs:

*Androecium.*—Present on disc florets only; no pollen.

*Gynoecium.*—Present on both ray and disc florets.

PLANT

A. General Appearance:

*Height.*—Medium; 25 to 35 cm as a pinched pot mum with 0 to 7 long days after pinch prior to short days and 1 application of 2500 ppm B-9 SP.

*Branching pattern.*—Semi-spreading.

B. Foliage:

*Color (upper surface).*—147A to 147B.

*Color (under surface).*—147B to 147C.

*Shape.*—Lobed and slightly serrated.

CHART A

Comparison of Raya and Quills

| CULTIVAR | RAY FLORET COLOR | CAPITULUM FORM & TYPE | BRANCHING PATTERN |
|---|---|---|---|
| Raya | White | Flat Spoon Daisy | Semi-spreading |
| Quills | White | Flat Spoon Daisy | Semi-upright |

| CULTIVAR | DIAMETER ACROSS FACE OF CAPITULUM | PLANT HEIGHT | FLOWERING RESPONSE PERIOD |
|---|---|---|---|
| Raya | Up to 13 cm | Medium | 8 weeks |
| Quills | 65–100 mm | Medium | 7 weeks |

| CULTIVAR | RECOMMENDED AS |
|---|---|
| Raya | Disbud |
| Quills | Disbud and spray |

COMPARISONS MADE OF PLANTS GROWN IN SALINAS, CALIFORNIA AND IN LEAMINGTON, ONTARIO, CANADA

I claim:

1. A new and distinct Chrysanthemum plant named Raya, as described and illustrated, and particularly characterized as to uniqueness by the combined characteristics of flat capitulum form; spoon daisy capitulum type; white ray floret color; diameter across face of capitulum of up to 13 cm at maturity when grown as a pinched disbudded pot mum; uniform eight week photoperiodic flowering response to short days; medium plant height when grown as a pinched pot mum; excellent tolerance to high and low temperatures; recommended as disbudded pot mum; and semi-spreading branching pattern.

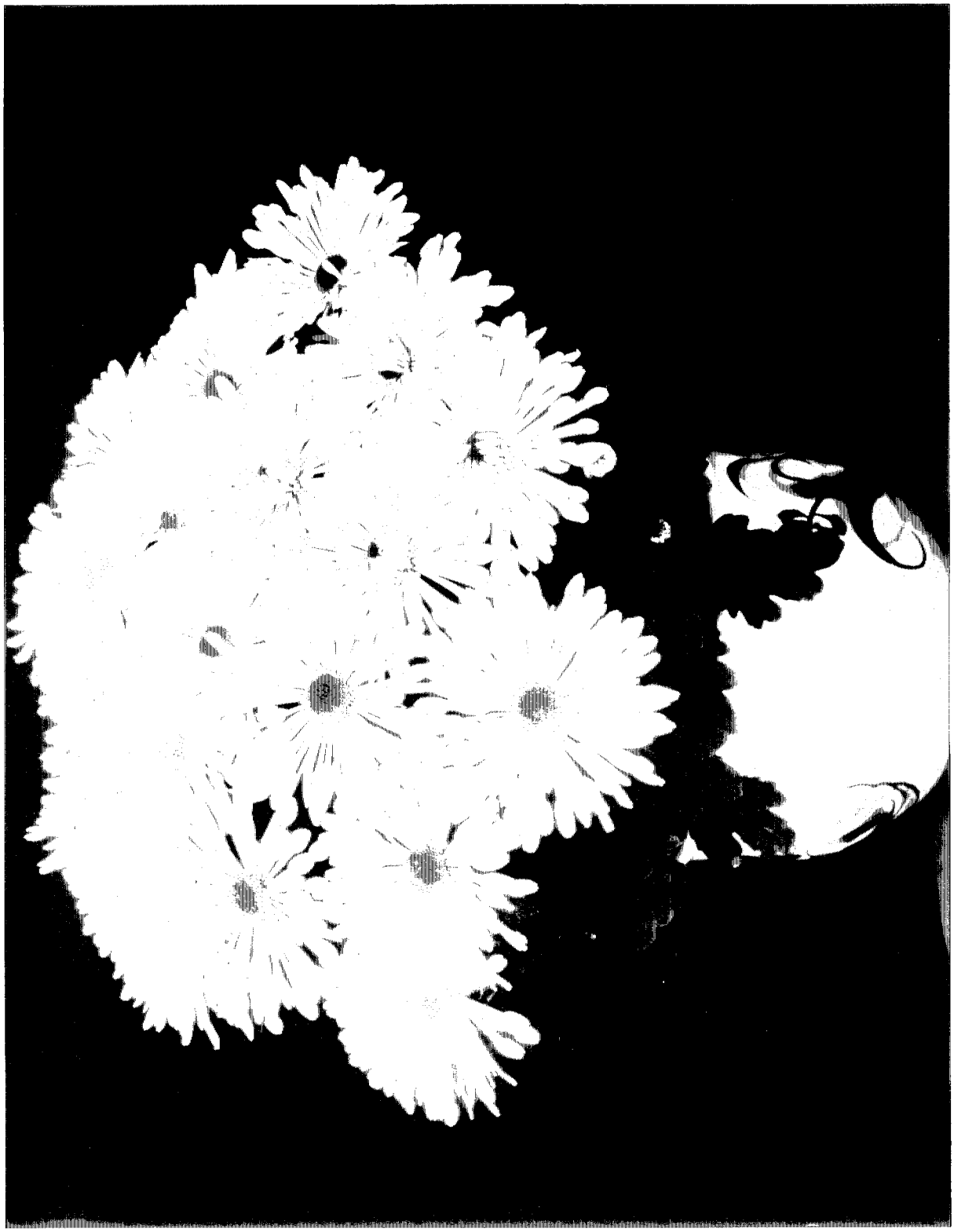

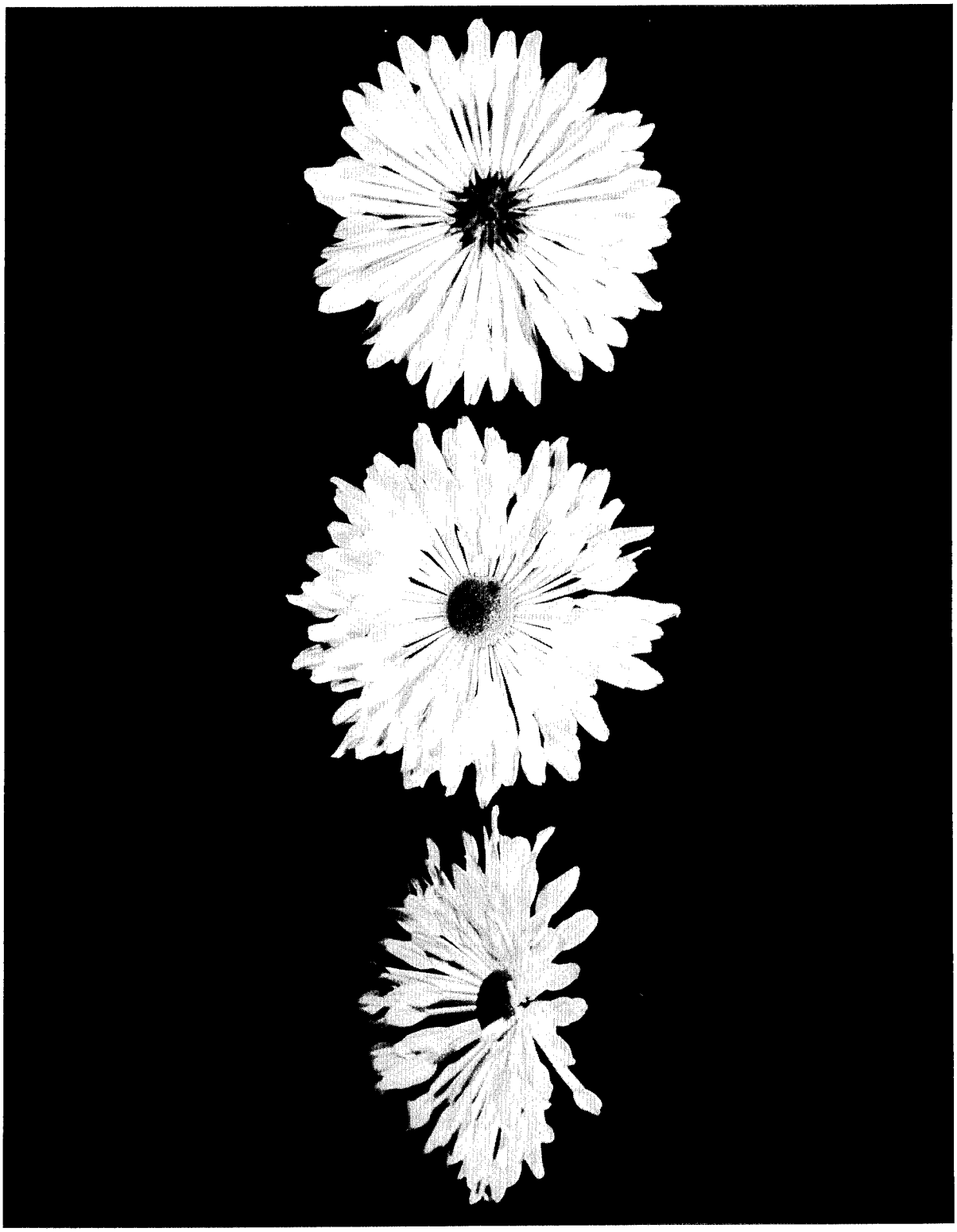

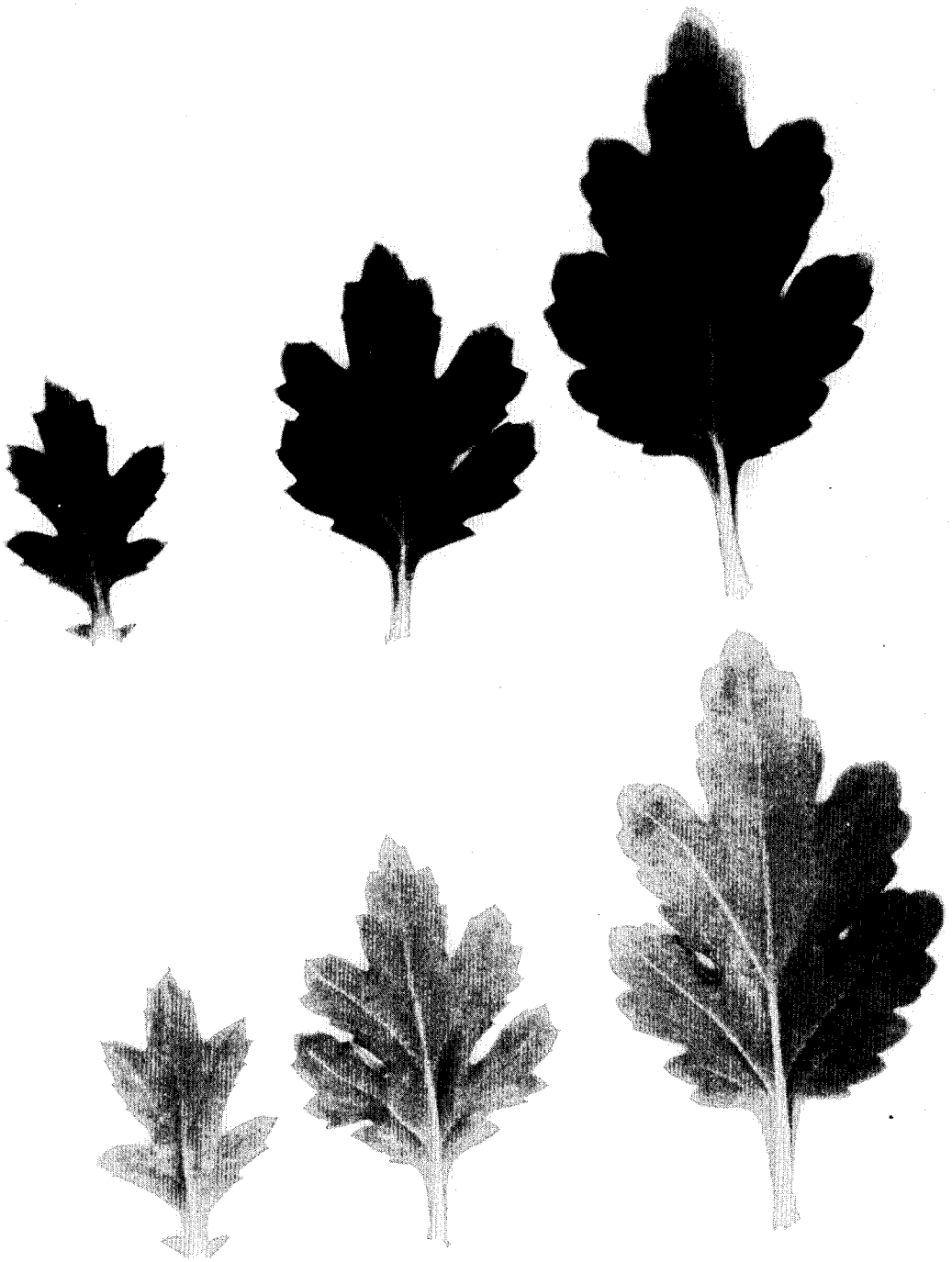

* * * * *